United States Patent [19]

Weyant

[11] Patent Number: 4,692,145
[45] Date of Patent: Sep. 8, 1987

[54] POWER SYSTEM FOR INFUSION PUMPS
[75] Inventor: Robert R. Weyant, Claremont, Calif.
[73] Assignee: American Hospital Supply Corporation, Deerfield, Ill.
[21] Appl. No.: 660,940
[22] Filed: Oct. 15, 1984
[51] Int. Cl.$^4$ .............................................. A61M 5/00
[52] U.S. Cl. ........................................ 604/65; 307/66
[58] Field of Search ............... 128/DIG. 12, DIG. 13, 128/302.14; 604/65–67, 151; 307/64–66

[56] References Cited
U.S. PATENT DOCUMENTS

| | | | |
|---|---|---|---|
| 4,181,842 | 1/1980 | Elias et al. | 307/66 |
| 4,307,789 | 12/1981 | Bertot | 307/66 X |
| 4,336,463 | 6/1982 | Beeghly | 307/66 |
| 4,354,118 | 10/1982 | Spencer | 307/66 |
| 4,451,742 | 5/1984 | Asmell | 307/66 |
| 4,467,844 | 8/1984 | DiGianfilippo et al. | 604/65 X |

FOREIGN PATENT DOCUMENTS 2533317 2/1976 Fed. Rep. of Germany ........ 604/65

Primary Examiner—Edward M. Coven
Attorney, Agent, or Firm—Weissenberger & Peterson

[57] ABSTRACT

A safety system for battery-operated, microprocessor-controlled infusion pumps using separate primary and reserve batteries. When the primary battery nears exhaustion, the reserve battery is switched in and an interval timer is started, but the pump operation is not interfered with. At the expiration of the timer interval, the pump is switched to a KVO mode to keep it in minimal operation as long as possible. When the reserve battery also nears exhaustion, the microprocessor is signalled to perform an orderly shutdown routine while battery power is still available. Audible alarms may be provided to apprise nursing personnel of the various phases in the system's operation.

12 Claims, 2 Drawing Figures

POWER SYSTEM FOR INFUSION PUMPS

This invention relates to a safety system for battery-operated infusion pumps.

BACKGROUND OF THE INVENTION

Infusion pumps for continuously providing a patient with accurately metered doses of various intravenous medications are normally connected to the commerical hospital power supply. In recent times, however, programmable record-keeping infusion pumps have been built which normally operate on AC power in conjuction with other apparatus, but which can be temporarily removed from the AC power supply, e.g. during transportation of a patient. Infusion pumps of this type are generally equipped with a microprocessor unit which governs the operation of the pump and keeps track of its performance. Operation of the pump with insufficient battery votage in these devices not only affects the accuracy of the medication delivery, but also interferes with the operation of the microprocessor in ways which can be potentially dangerous to the patient. On the other hand, it is undesirable to require nursing personnel to monitor the battery level, because battery operation most of the time is short encough to never raise problems of battery exhaustion.

It is consequently desirable to provide a battery power supply for this type of unit which allows non-emergency remedial action when the battery power runs low, yet maintains the system in at least minimal operational condition for as long as possible if no remedial action is taken.

SUMMARY OF THE INVENTION

The present invention provides a system of the type described by using two batteries which are independently connectable to power the infusion pump. As long as the primary battery voltage is up to par, the primary battery is the only power source for the pump. When the output voltage of the primary battery starts to drop below a predetermined safe level, the system switches in the reserve battery, either alone or in parallel with the primary battery. The infusion pump continues to operate in this reserve mode for a predetermined interval of time which is so calculated as to safely provide adequate power, from the reserve battery alone if necessary, to operate the infusion pump during the entire interval even at its highest possible operating speed. Upon the expiration of this fixed safe interval (during which any remedial action would normally be taken), the system switches the infusion pump to the minimum speed required to keep the patient's vein open. The system remains in that condition until the reserve battery voltage (or the combined voltage of the primary and reserve battery, as the case may be) drops below a safe level. At that time, the system takes the microprocessor through an orderly shutdown routine and stops the pump.

In a further aspect of the invention, the system operates a series of alarm indicators which provide alarm signals of increasing urgency through the various steps of the system's operation. For example, a low-volume tone of pleasant pitch may be used during the fixed time interval during which remedial action would normally be taken. A louder tone of harsher pitch may be used during the "keep vein open" (KVO) period during which the patient is not receiving an adequate level of medication but is not otherwise affected. A loud tone of harsh pitch may finally be used upon shutdown to alert nursing personnel to the need for immediate major attention.

Because the primary battery triggers the reserve mode when its output voltage drops under full load conditions, it still has some reserve power for extended operation under KVO conditions. Consequently, it is advantageous to connect both batteries in parallel during the reserve mode. However, provisions must be made in accordance with the invention to prevent the reserve battery from draining into the primary battery in case of an internal failure of the primary battery.

DESCRIPTION OF THE PREFERRED EMBODIMENT

Figure 1:
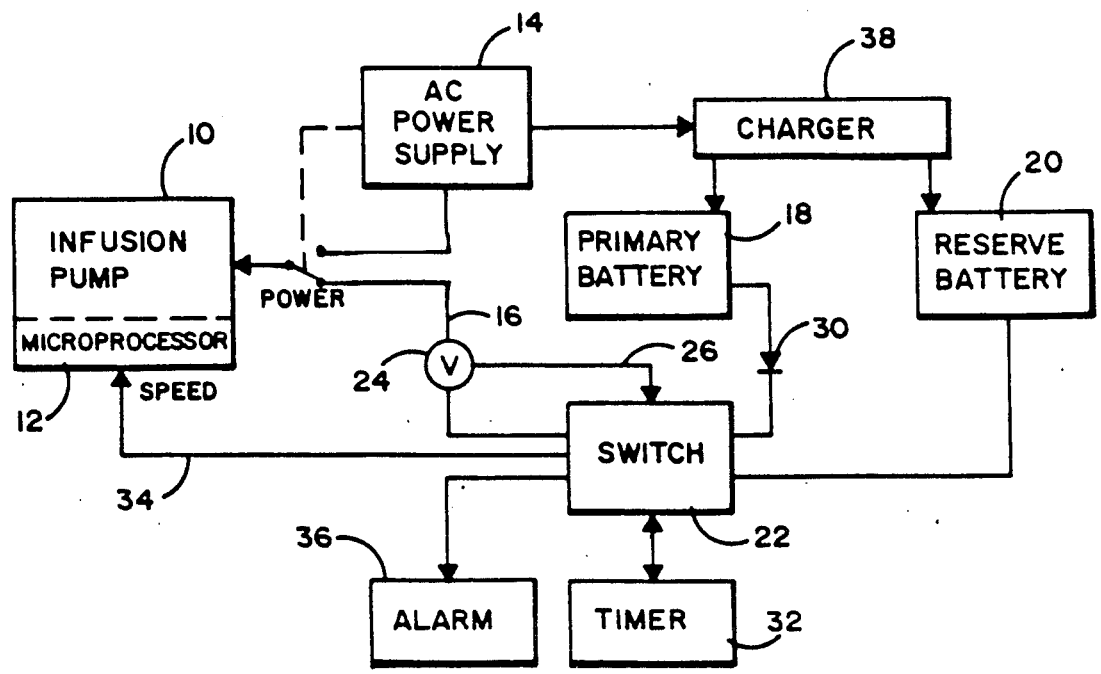
FIG. 1 is a block diagram of the safety system of this invention.

In FIG. 1, the infusion pump 10 may be equipped with a microprocessor 12 which normally controls its speed and other operational parameters in accordance with a pre-stored program. The microprocessor 12 also keeps track of the pump's performance and keeps records of the amount of medication delivered.

Figure 2:
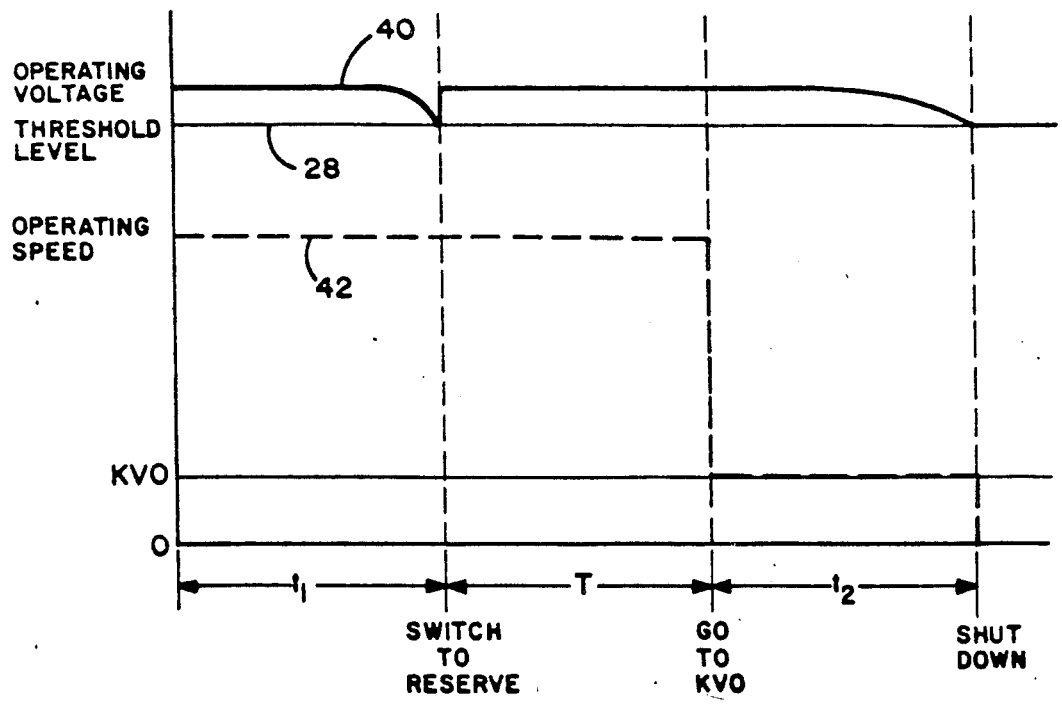
FIG. 2 is a time-amplitude diagram illustrating the power bus voltage and speed of the pump at various times in the operation of the system.

Whenever the normal AC power supply 14 is inoperative or disconnected, the pump 10 is powered through a power bus 16 supplied with battery power from primary battery 18 and/or reserve battery 20 in accordance with the setting of switch 22. The power bus 16 is provided with a voltage monitor 24 which actuates switch 22 over line 26 whenever the voltage in power bus 16 drops below a predetermined threshold level 28 (FIG.2). The threshold level 28 preferably represents the lowest DC voltage at which the pump 10 and its microprocessor 12 can still function reliably at maximum pump speed.

Normally, the switch 22 connects the primary battery 18 to the power bus 14 and does not interfere with the normal operation of the pump 10 by microprocessor 12. When, however, the voltage of power bus 16 drops below the threshold level 28 to the impending exhaustion of primary battery 18, the monitor 24 actuates switch 22 over line 26 to switch the reserve battery 20 onto power bus 16, preferably but not necessarily in parallel with the primary battery 18. A protective circuit schematically indicated in FIG.1 by diode 30 prevents reserve battery 20 from discharging into primary battery 18 while the two batteries are connected in parallel.

In a typical embodiment, the primary battery may be a 6 volt battery with 2 ampere-hour capacity, the reserve battery may be a 6 volt battery with 0.5 ampere-hour capacity, and the threshold level may be on the order of 5.5 volts.

The exhaustion of the primary battery 18 is a function of the speed of pump 10 as dictated by the microprocessor 12, and of the charge state of the primary battery 18. Consequently, it is impossible to predict with any accuracy how long the primary battery 18 can power the pump 10 before it is exhausted. Likewise, the exhaustion of reserve battery 20 is unpredictable, and provisions must be made to assure proper operation of the safety system of this invention in a worst-case situation.

The original actuation of switch 22 by the exhaustion of the primary battery 18 causes the switch 22 to start the interval timer 32. The timer 32 is set to run for a fixed interval, e.g. fifteen minutes. The timer interval is so calculated as to assure normal operation of the pump 10 and microprocessor 12 at the highest speed to which pump 10 can be set, without danger of exhausting the reserve battery 20. (Normally, the batteries 18 and 20 would be maintained at or near full charge while AC power is available.)

At the expiration of the fixed time interval, timer 32 actuates switch 22 so as to signal microprocessor 12 over line 34 to reduce the speed of pump 10 to the lowest speed which will maintain sufficient flow to keep the patient's vein open (KVO mode). In this condition, pump 10 and microprocessor 12 exert the least possible drain on the battery system. Consequently, depending on the remaining charge in battery 18 and/or 20, the pump may be able to operate in the KVO mode for a substantial period of time.

Eventually, however, the reserve battery 20 also becomes exhausted if no remedial action is taken. When the monitor 24 senses a voltage drop in the power bus 16 below the threshold level 28 for the second time (or below another appropriate predetermined level), the system knows that a power failure is imminent, and that an orderly shutdown of the pump 10 and microprocessor 12 is necessary. Consequently, upon receiving the second low-voltage signal from monitor 24 over line 26, switch 22 instructs microprocessor 12 over line 34 to store its data and shut down the pump 10 in a non-injurious manner. Sufficient power remains in the batteries at this point to take the microprocessor 12 and pump 10 through the shutdown procedure.

In accordance with a further aspect of the invention, the switch 22 may also actuate an alarm 36 when an operator's intervention is needed. Preferably, the alarm 36 provides, in addition to any visual indications, audible indication which varies with the seriousness of the alarm condition. For example, when the primary battery is exhausted and the system switches to the reserve mode, the alarm 36 may be set to produce a soft, relatively pleasing tone which is sufficient to alert a nurse in the patient's room but not to disturb the patient.

If no remedial action is taken and the tmer 32 times out, the volume of the alarm may be increased and its pitch may be made harsher to alert the nursing personnel that the patient is no longer receiving medication at the proper rate. Finally, upon shutdown of the pump, the alarm may be made quite loud and harsh to alert the nursing personnel even outside the patient's room that immediate action is required. Preferably, the alarm 36 is separately powered, or else operable at very low battery voltages, so as to continue functioning for a sustantial length of time after the pump 10 has been shut down.

The batteries 18 and 20 are preferably rechargeable batteries so that they may be kept fully charged by the charger 38 whenever the AC power supply 14 is connected and operational. Appropriate circuitry (not shown) may be included to reset the switch 22 to its normal position whenever AC power is present.

FIG. 2 illustrates the voltage of power bus 16 at 40 and the speed of pump 10 at 42. As mentioned above, the times $t_1$ and $t_2$ vary from cycle to cycle of the system's operation depending on the batteries' load and charge status, whereas the interval T is fixed.

It will be seen that the invention provides a safety system for infusion pumps which allows a fixed time for remedial action upon exhaustion of the primary battery 18; which thereafter maintains the pump in a minimally operational (KVO) mode for as long as possible; and which finally assures an orderly shutdown of the pump just before the battery power becomes totally exhausted.

I claim:

1. The method of providing operational safety for a variable-speed, battery operated infusion pump, comprising the steps of:
   (a) operating said pump at normal operating speed substantially above the KVO speed in a primary mode wherein said pump is powered by a primary battery, as long as the primary battery voltage remains above a predetermined threshold level;
   (b) operating said pump at normal operating speed in a reserve mode wherein said pump is powered at least by a reserve battery for a predetermined time interval after said primary battery voltage drops below said threshold;
   (c) operating said pump at said KVO speed under reserve battery power following said interval.

2. The method of claim 1, further comprising the step of shutting down said pump when the voltage powering said pump in said reserve mode drops below a predetermined threshold.

3. The method of claim 1, in which said pump is powered by both the primary and the reserve battery in said reserve mode.

4. The method of claim 3, further comprising the step of preventing current from being drawn by said primary battery from said reserve battery.

5. A safety system for an infusion pump which can be powered by first and second batteries, comprising:
   (a) a variable speed infusion pump;
   (b) switch means having a first condition in which said first battery is connected to power said pump, a second condition in which at least said second battery is connected to power said pump, and third condition in which said pump is caused to operate by said second battery at reduced speed;
   (c) voltage sensing means connected to said switch means to produce an actuation of said switch means switching it from said first condition to said second condition when the voltage of the battery power supplied to said pump drops below a predetermined level; and
   (d) timing means responsive to said actuation for switching said switch means to said third condition after a predetermined time interval following said actuation.

6. The system of claim 5, in which:
   (e) in said first condition of said switch means, said pump is powered in a primary mode by said first battery at normal operating speed;
   (f) in said second condition of said switch means, said switch means
     (i) switch said pump to a reserve mode in which said pump is powered by at least said second battery;
     (ii) maintain said pump at normal operating speed; and
     (iii) start said timing means; and
   (g) in said third condition of said switch means, said switch means reduce the speed of said pump to a KVO level.

7. The system of claim 6, in which said switch means have a fourth condition in which said pump is shut down, and said switch means switch to said fourth condition when the voltage of the battery power supplied to said pump drops below a predetermined value while said switch means is in said third condition.

8. The system of claim 7, further comprising alarm means operatively connected to said switch means for indicating an alarm condition whenever said pump is powered by said second battery, said alarm means being arranged to continue functioning substantially beyond the shutdown of said pump.

9. The system of claim 5, in which said pump is powered by both said batteries during the reserve mode.

10. The system of claim 9, further comprising protection means for preventing said first battery from drawing current from said second battery.

11. The system of claim 5, further comprising alarm means operatively connected to said switch means for indicating an alarm condition whenever said pump is powered by said second battery.

12. The system of claim 11, in which said alarm means are arranged to produce alarm signals of increasingly attention-demanding nature upon each actuation of said switch means.

* * * * *